United States Patent [19]

Chan et al.

[11] Patent Number: 6,087,105

[45] Date of Patent: Jul. 11, 2000

[54] GENE ENCODING INVASION PROTEIN OF CAMPYLOBACTER SPECIES

[76] Inventors: Voon Loong Chan, 93 Elm Ridge Drive, Toronto, Ontario, Canada, M6B 1A6; Angela Joe, #1122, 341 Bloor Street West, Toronto, Ontario, Canada, M5S 1N8; Yuwen Hong, 300 Regina Street North, Waterloo, Ontario, Canada, N2J 4H2

[21] Appl. No.: 09/056,783

[22] Filed: Apr. 8, 1998

Related U.S. Application Data

[60] Provisional application No. 60/043,414, Apr. 8, 1997.

[51] Int. Cl.[7] .......................................................... C12Q 1/68
[52] U.S. Cl. ......................... 435/6; 424/282.1; 435/69.7; 536/23.5
[58] Field of Search .............................. 424/282.1; 435/6, 435/69.7; 536/23.5

[56] References Cited

U.S. PATENT DOCUMENTS

| | | | |
|---|---|---|---|
| 5,681,942 | 10/1997 | Buchwald et al. | 536/23.5 |
| 5,719,044 | 2/1998 | Shoseyov et al. | 435/69.7 |
| 5,744,307 | 4/1998 | Kuroda et al. | 435/6 |
| 5,869,066 | 2/1999 | Pace et al. | 424/282.1 |

OTHER PUBLICATIONS

Pei et al, J Biological Chemistry, vol. 268, Sep. 5, pp. 18717–18725, 1993.
Grant, CCR et al, Infection and Immunity, May 1993, vol. 61(5), pp. 1764–1771.
Ketley, J.M., J. Med. Microbiol., vol. 42, pp. 312–327, 1995.
Bourke, B. et al, Microbiology, vol. 141, pp. 2417–2424, 1995.
Pesci, EC et al, Infection and Immunity, vol. 62, (7), Jul. 1994, pp. 2687–2694.
Yao, R et al, Mol. Microbiol., vol.14(5), pp. 883–893, 1994.
Boot, HJ et al, Mol. Microbiol. vol. 21(6), Sep. 1996, pp. 1117–1123.
Beveridge, TJ et al, FEMS Microbiol. Reviews, vol. 20, pp. 99–149, 1997.
Altschul, S. F. et al. *J. Mol. Biol.* 215:403–410, 1990.
Bourke, B., et al., *Microbiol.* (UK) 141:2417–2424, 1995.
Chan V.L. and Bingham H.L., *Gene* 101:51–58,1991.
Chan, V. L., et al. *Gene* 164:25–31, 1995.
Chang, N., and D. E. Taylor. *J. Bacteriol.* 172:5211–5217, 1990.
Grant, C. C. R., et al., *Infect. Immun.* 61:1764–1771, 1993.
Hani, E. K., and V. L. Chan. *J. Bacteriol.* 177:2396–2402, 1995.
Hong, Y., et al., *Microbiol.* (UK) 141:2561–2567, 1995.
Ketley, J. M. *J. Med. Microbiol.* 42:312–327, 1995.
Kim, N.W. et al. *Gene* 164:101–106, 1995.
Kim, N. W., et al. *J. Bacteriol.* 175:7468–7470, 1993.
Kim, N. W., et al. *J. Bacteriol.* 174:3494–3498, 1992.
Labigne–Roussel, A., et al. *J. Bacteriol.* 170:1704–1708, 1988.
McClelland, H., et al. *Nucl. Acids Res.* 15:5985–6005, 1987.
Mecsas, J., and E. J. Strauss. *Emerg. Infect. Dis.* 2:271–288, 1996.
Pesci, E.C., et al. *Infect. Immun.* 62:2687–2694, 1994.
Rosqvist, R., et al. *EMBO J.* 13:964–972, 1994.
Sory, M. P., and G. R. Cornelis. *Mol. Microbiol.* 14:583–594, 1994.
Yao, R., et al. *Mol. Microbiol.* 14:883–893, 1994.
Walker, R.I. et al. *Microbiol. Rev.* 50(1):81–94, 1986.
Wang, Y., and D. E. Taylor. *J. Bacteriol.* 172:949–955, 1990.
Wassenaar, T. M., et al. *Infect. Immun.* 62:3901–3906, 1994.
Watarai, M., et al. *EMBO J.* 14:2461–2470, 1995.
Zierler, M. K., and J. E. Galan. *J. Infect. Immun.* 63:4024–4028, 1995.

*Primary Examiner*—James C. Housel
*Assistant Examiner*—Ginny Allen Portner
*Attorney, Agent, or Firm*—Bereskin & Parr

[57] ABSTRACT

A protein associated with adherence and invasion of Campylobacter spp. including *C. jejuni* and *C. coli* is provided. Methods are disclosed for detecting Campylobacter spp. including *C. jejuni* and *C. coli* in a biological sample by determining the presence of the protein or a nucleic acid molecule encoding the protein in the sample. Compositions for treatment of infections diseases and vaccines are also described.

4 Claims, 6 Drawing Sheets

FIGURE 1

```
CTTTAATTAAAGTTTATTTTTGATAATATATTTAAATTTCATGACATTTAAATATTTATGAATTA                    65
                                         -35
TATATAAATTAAATACAATTAAAAGAGGTTAT ATGCAAAATC TTTTACTCTA TATAAAAAAT                    127
    -10                     SD    M  Q  N    L  L  L  Y   I  K  N                    10
AACCTAACTC CAACCCTAGC TCAAATTCTT TTACAAGCTT TAAAAAATTC GAATAATGAA                    187
 N  L  T    P  T  L    Q  I  L    L  Q  A    L  K  N  S   N  N  E                    30
AAATTTTTTA CCTTTGTTTT GAAAAATATT GAAACAATTT GCACTTGGCT CAATTCTAAC                    247
 K  F  F    T  F  V  L  K  N  I    E  T  I    C  T  W  L   N  S  N                   50
GAATTTAGGG ATAGATATTT ATCAACAAAA CATCCTTATC CACCTTTAAT CAATCCTAAT                    307
 E  F  R    D  R  Y  L  S  T  K    H  P  Y    P  P  L  I   N  P  N                   70
TTTATAGAAA TAGATTCTAG TCGACATTGC GCAGAATTAG CTTGGGATTT AAATTTACCC                    367
 F  I  E    I  D  S  S  R  H  C    A  E  L    A  W  D  L   N  L  P                   90
CTACCTAAAC ACTATAAATT TATCTATATT TCTCCACATG GCGTTGGAGC AGCAGCATTT                    427
 L  P  K    H  Y  K  F  I  Y  I    S  P  H    G  V  G  A   A  A  F                  110
TTAAGATACC TTAATCAATG TTGCGATGTA ACTTGTTTTG CCTCCTGGGT TTTACCACCT                    487
 L  R  Y    L  N  Q  C  C  D  V    T  C  F    A  S  W  V   L  P  P                  130
GATAGCAAAG AGAGATATTG TATTAATTAC ATGTGTCTAA ATGATAATAC AATTGCTCAA                    547
 D  S  K    E  R  Y  C  I  N  Y    M  C  L    N  D  N  T   I  A  Q                  150
TATGCTATTA ATATATCAGA AATTAATCTA CCTTATTTTG ATAAATATCT ATCTTTATTA                    607
 Y  A  I    N  I  S  E  I  N  L    P  Y  F    D  K  Y  L   S  L  L                  170
GATTTTAATT CTAAGATTAT TTGCGGAGTT CGAGATCCAA TAGGACTTTT AAAGCATAGC                    667
 D  F  N    S  K  I  I  C  G  V    R  D  P    I  G  L  L   K  H  S                  190
TGGGGAAGAG ATTGGAGTAA AGTTTTAAGA AACTATCCCC CTGAATTTAA TCTAACTTAT                    727
 W  G  R    D  W  S  K  V  L  R    N  Y  P    P  E  F  N   L  T  Y                  210
GATTGGCGTT ATTACATCAA CTATCTTACT CATCAAAATC ATAAAATTAA AATCGATATA                    787
 D  W  R    Y  Y  I  N  Y  L  T    H  Q  N    H  K  I  K   I  D  I                  230
AATGAACTAC AACAAGGAGT TTTTATCATC TCTTATTTAT TAAAATATTT TAACAAAGAC                    847
 N  E  L    Q  Q  G  V  F  I  I    S  Y  L    L  K  Y  F   N  K  D                  250
AATGTATACT ATCTTGATAT GGAAGAAATC CGCCAATCAA AGGCCTTCGA TACCATGAAT                    907
 N  V  Y    Y  L  D  M  E  E  I    R  Q  S    K  A  F  D   T  M  N                  270
TTACTTGCTA TAAATTTTAA TTTTACCCCC CCCCATAAAG ATAAATTAGA TTTATTTAAA                    967
 L  L  A    I  N  F  N  F  T  P    P  H  K    D  K  L  D   L  F  K                  290
ATTAAAGAAT TTAGAGGTTA TATTCGCTAT CTTTTTCCTA TTACACTTTA TGCAAATTCT                   1027
 I  K  E    F  R  G  Y  I  R  Y    L  F  P    I  T  L  Y   A  N  S                  310
AAAGATATTA ATAACACCTT TTATCTTAAT ACTCCTAAAA ATAATAAAAA TTTCAATATT                   1087
 K  D  I    N  N  T  F  Y  L  N    T  P  K    N  N  K  N   F  N  I                  330
GATAGAACTT CTAGCATTCC CATAATTTTA GACAGAAAAC ATATCAATCA TGAAAAAATA                   1147
 D  R  T    S  S  I  P  I  I  L    D  R  K    H  I  N  H   E  K  I                  350
GACATAATAC AAGAAATTAT AAAAAACGAC CTATGTAATG ATATGGGTGT ATATATTGAT                   1207
 D  I  I    Q  E  I  I  K  N  D    L  C  N    D  M  G  V   Y  I  D                  370
AAAAATGATT TTAAGCAATT AGAACAAAAC AATCTTTTAT TTTCAACAAT TAAACATTAT                   1267
 K  N  D    F  K  Q  L  E  Q  N    N  L  L    F  S  T  I   K  H  Y                  390
TTGTATGATT TTTTATATCA AATTAAAATA ACCATAGATG AAACAGAATC AAAAATGATG                   1327
 L  Y  D    F  L  Y  Q  I  K  I    T  I  D    E  T  E  S   K  M  M                  410
AAAGAAAAAG ATGTAATAGA TTATTTTATA AAAAATAAAT CACTTATTTA CACTTTTTTT                   1387
 K  E  K    D  V  I  D  Y  F  I    K  N  K    S  L  I  Y   T  F  F                  430
AATATTTTTG AAAATGAACT AAATCATTTA AAACAAACAC ATCCTCATAT TATTGATTCT                   1447
 N  I  F    E  N  E  L  N  H  L    K  Q  T    H  P  H  I   I  D  S                  450
TGGAAATATT ATAAAGAATT TGAAAAAATA TACAAAGATA AATAA TCATATCACTTACAC                   1507
 W  K  Y    Y  K  E  F  E  K  I    Y  K  D    K  *                                  464
AAAATCAATAGGATC                                                                     1522
```

FIGURE 3
-200
-116
-97
-66
-42

GENE ENCODING INVASION PROTEIN OF CAMPYLOBACTER SPECIES

This application claims benefit from U.S. provisional application Ser. No. 60/043,414 filed on Apr. 8, 1997 now abandoned.

FIELD OF THE INVENTION

The invention relates to novel nucleic acid molecules encoding a protein involved in the virulence of bacteria and more particularly of *Campylobacter jejuni*; the novel proteins encoded by the nucleic acid molecules; and, uses of the proteins and nucleic acid molecules.

BACKGROUND OF THE INVENTION

*Campylobacter jejuni* (*C. jejuni*), a gram-negative microaerophilic bacterium, is a leading cause of bacterial diarrhea and enterocolitis in children and adults in both developing and developed countries (Walker R I et al, Microbiol. Rev. 50(1): 81–94, 1986; Kim N W et al, J. Bacteriol. 174(11):3494–3498, 1992; Chan V L and Bingham H L, Gene 101:51–58, 1991). Clinical symptoms of Campylobacter infections range from watery diarrhea to inflammatory dysentery and bloody diarrhea (Cover T L and Blaser N J, Ann. Rev. Ned. 40:269–285, 1989; Walker R I et al, supra). Complications from *C. jejuni* infections have included Guillain-Barré syndrome, a neurological disease which may lead to respiratory paralysis and death, toxic megacolon, acute mesenteric adenitis syndrome, and reactive arthritis (Kaldor J and Speed B R, British Medical J. 288:1867–1870, 1984; Johnson K et al, Acta. Med. Scand. 214:165–168, 1983; Walker R I et al, supra).

*C. jejuni* is commonly found in surface water, in animals such as cattle, sheep, goats, swine and poultry, in industrial wastes, and in many different types of foods including unpasteurized dairy products. Human pets such as dogs, cats and birds may also be infected with *C. jejuni* and may transmit the bacterium to humans. (Cover T L and Blaser M J, Ann. Rev. Med. 40:269–285, 1989; and Penner, J. L., Clin. Micro. Rev. 1:157–172, 1988).

Despite recognition of *C. jejuni* as a major human enteropathogen, an understanding of both the genetic organization and virulence mechanisms of this organism remains rudimentary. Campylobacteria have small genomes with a low-percent G+C and high A+T content. For instance, the *C. jejuni* TGH9011 chromosome is 1812 kb in size with a G+C content of approximately 30%. Within this A+T-rich genome, restriction enzyme sites high in G+C such as SacII (CCGGCC) and SmaI (CCCGGG) are infrequently found (Kim, 1992). On the basis of its size and G+C content, A *C. jejuni* chromosome should contain approximately 110 SalI (GTCGAC) recognition sites (McClelland, 1987). Surprisingly, all of the *C. jejuni* isolates analyzed to date contain only 5–6 SalI sites (Chang & Taylor 1990; Kim et al., 1992), and three of these sites are located within 23S rRNA encoding sequences (Kim et al.,1993; Kim et al., 1995). The three recognition sites for the enzyme SalI are each located within a conserved rRNA operon.

SUMMARY OF THE INVENTION

The present inventors have identified and characterized a novel SalI site-containing a non-rRNA gene from *C. jejuni* TGH9011. The protein encoded by this gene is comprised of 464 amino acids with a predicted molecular weight of 55,651. No significant homology to other known proteins was found in a database search. Maxicell analysis revealed the synthesis of a cloned gene product with an apparent molecular mass of 55 kDa.

A site-specific insertional mutation within the gene reduced the ability of *C. jejuni* to adhere to and invade the human intestinal cell line INT407. The gene was designated cipA (Campylobacter invasion phenotype). Mapping studies indicate that cipA is a linking gene for a previously unrecognized SalI PFGE restriction fragment (denoted SalI F) on the physical map of *C. jejuni*.

Accordingly, in its broad aspect, the present invention provides a purified and isolated nucleic acid molecule comprising a sequence encoding a protein associated with invasion of virulent bacteria.

In one embodiment, the present invention provides an isolated nucleic acid molecule having a sequence encoding a protein associated with adherence and invasion of Campylobacter spp.

According to one embodiment, the present invention provides a purified and isolated nucleic acid molecule comprising a sequence encoding a protein associated with invasion by *C. jejuni*.

According to another embodiment, the present invention provides a purified and isolated nucleic acid molecule comprising a sequence encoding a protein associated with invasion by *C. coli*.

In a preferred embodiment, a purified and isolated nucleic acid molecule is provided having a sequence which encodes a protein associated with invasion by *C. jejuni* (this protein is encompassed within the terms "CipA protein" or "CipA proteins" used herein). The nucleic acid molecule having a nucleic acid sequence as shown in FIG. 1 and in the Sequence Listing as SEQ ID NO: 1 and the protein having an amino acid sequence as shown in FIG. 1 and in the Sequence Listing as SEQ ID No: 2. Most preferably, the purified and isolated nucleic acid molecule comprises: (a) a nucleic acid sequence as shown in SEQ ID NO: 1 and FIG. 1, wherein T can also be U; (b) nucleic acid sequences complementary to (a); (c) nucleic acid sequences which are homologous to (a) or (b); or, (d) a fragment of (a) to (c) that is at least 15 bases, preferably 20 to 30 bases, and which will hybridize to (a) to (c) under stringent hybridization conditions.

The invention also contemplates a purified, isolated nucleic acid molecule comprising a sequence encoding a truncation of a protein of the invention, an analog, or a homolog of a protein of the invention, or a truncation thereof (herein collectively referred to as "CipA protein" or "CipA proteins").

According to one embodiment, the invention provides a purified and isolated polypeptide having an amino acid sequence of a CipA protein associated with adherence and invasion of Campylobacter spp. Preferably the Campylobacter species is *C. Jejuni* or *C. Coli*.

The nucleic acid molecules of the invention may be inserted into an appropriate expression vector, i.e., a vector which contains the necessary elements for transcription and translation of the inserted protein-coding sequence. Accordingly, recombinant DNA molecules adapted for transformation of a host cell may be constructed which comprise a nucleic acid molecule of the invention operatively linked to an expression control sequence. A transformant host cell including a recombinant molecule of the invention is also provided. Still further, this invention provides plasmids which comprise recombinant molecules of the invention.

The present invention further relates to an avirulent strain of *C. jejuni* comprising an avirulent bacterial carrier strain transformed with a recombinant molecule of the invention, and a vaccine composition comprising a bacterial carrier strain transformed with a recombinant molecule of the invention.

The invention also provides a method of preparing a CipA protein of the invention utilizing a nucleic acid molecule of the invention. In an embodiment a method for preparing a CipA protein of the invention is provided comprising: (a) transferring a recombinant expression vector of the invention into a host cell; (b) selecting transformed host cells from untransformed host cells; (c) culturing a selected transformed host cell under conditions which allow expression of the protein; and (d) isolating the protein.

The invention still further provides a purified and isolated polypeptide having part or all of the primary structural conformation (ie., a continuous sequence of amino acid residues) and the activity of CipA. In a preferred embodiment the polypeptide has an amino acid sequence as shown in FIG. 1 and in the Sequence Listing as SEQ ID NO: I and SEQ ID NO: 2, or a sequence having between 40-50 percent homology thereto. The invention also includes truncations of such purified and isolated polypeptide and analogs, homologs, and isoforms of the polypeptide and truncations thereof (herein collectively, also included in the terms "CipA protein" or "CipA proteins").

According to a further embodiment the present invention provides a protein encoded by the purified and isolated nucleic acid molecule having a nucleic acid sequence as identified in SEQ ID NO: 1.

The proteins of the invention may be conjugated with other molecules, such as proteins, to prepare fusion proteins. This may be accomplished, for example, by the synthesis of N-terminal or C-terminal fusion proteins.

The invention also relates to an antibody specific for one or more epitopes of a protein of the invention, preferably a monoclonal antibody and methods for preparing the antibodies. A method for detecting Campylobacter spp. as well as *C. jejuni* in a sample is provided comprising assaying for CipA protein in the sample. In an embodiment of the invention the method comprises contacting the sample with an antibody of the invention which is capable of being detected after it becomes bound to CipA in the sample, and measuring the amount of antibody bound to CipA in the sample, or unreacted antibody.

According to one embodiment the invention provides a monoclonal or polyclonal antibody specific for an epitope of the purified and isolated CipA polypeptide. An antibody provided in accordance with the invention can be one which binds a distinct epitope in an unconserved region of the polypeptide.

A kit for detecting Campylobacter spp. as well as *Campylobacter jejuni* in a sample comprising an antibody of the invention, preferably a monoclonal antibody and directions for its use is also provided. The kit may also contain reagents which are required for binding of the antibody to a CipA protein in the sample.

The nucleic acid molecules of the invention allow those skilled in the art to construct nucleotide probes for use in the detection of nucleotide sequences in samples such as biological, food, or environmental samples. The nucleotide probes may be used to detect nucleotide sequences that encode polypeptides related to or analogous to the CipA polypeptide of the invention.

Accordingly, the invention provides a method for detecting the presence of a nucleic acid molecule having a sequence encoding a polypeptide related to or analogous to a polypeptide of the invention, comprising contacting the sample with a nucleotide probe which hybridizes with the nucleic acid molecule, to form a hybridization product under conditions which permit the formation of the hybridization product, and assaying for the hybridization product.

The invention further provides a kit for detecting the presence of a nucleic acid molecule having a sequence encoding a polypeptide related to or analogous to a polypeptide of the invention, comprising a nucleotide probe which hybridizes with the nucleic acid molecule, reagents required for hybridization of the nucleotide probe with the nucleic acid molecule, and directions for its use.

The nucleic acid molecules of the invention also permit the identification and isolation, or synthesis, of nucleotide sequences which may be used as primers to amplify a nucleic acid molecule of the invention, for example in the polymerase chain reaction (PCR).

Accordingly, the invention relates to a method of determining the presence of a nucleic acid molecule having a sequence encoding a CipA protein or a predetermined part of a CipA protein in a sample, comprising treating the sample with primers which are capable of amplifying the nucleic acid molecule, in a polymerase chain reaction to form amplified sequences, under conditions which permit the formation of amplified sequences, and, assaying for amplified sequences.

The invention further relates to a kit for determining the presence of a nucleic acid molecule having a sequence encoding a CipA protein or a predetermined part of the protein in a sample, comprising primers which are capable of amplifying the nucleic acid molecule in a polymerase chain reaction to form amplified sequences, reagents required for amplifying the nucleic acid molecule thereof in an amplification reaction, preferably the polymerase chain reaction, means for assaying the amplified sequences, and directions for its use.

The nucleic acid molecules of the invention may also be used to assay for a substance which inhibits adherence or invasion of Campylobacter spp. including *C. jejuni*. Accordingly, the invention provides a method for assaying for a substance that interferes with a CipA protein. The method may be used, for example, to assay for a substance which affects the growth or pathogenicity of *C. jejuni*.

The substances identified using the method of the invention, antibodies, and antisense molecules may be used to reduce adherence and/or invasion of Campylobacter spp. including *C. jejuni* and accordingly may be used in the treatment of infectious diseases caused by Campylobacter spp. including *C. jejuni*. Accordingly, the substances may be formulated into pharmaceutical compositions for adminstration to subjects.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF DRAWINGS

The invention will now be described in relation to the drawings:

FIG. 1 shows the sequence of the orfS (cipA) gene and its flanking regions obtained from *C. jejuni* genomic DNA library clone E3-8 and the deduced amino acid sequence is indicated in single letter code below the nucleotide sequence SEQ ID NO: 1 and SEQ ID NO: 2;

FIG. 3 shows maxicell analysis for the elucidation of the plasmid-encoded proteins;

DETAILED DESCRIPTION OF PREFERRED EMBODIMENTS

Figure 2:
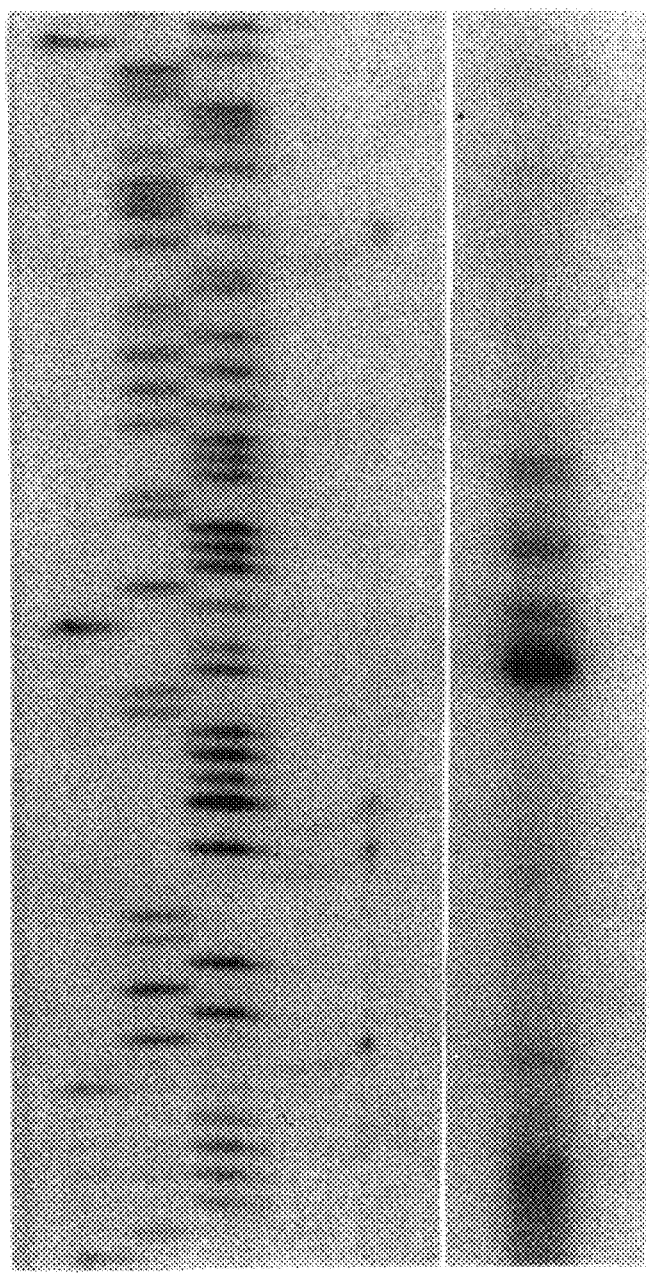
FIG. 2 is a primer extension mapping of the transcription start site of the orfS (cipA) mRNA.

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

For ease of explanation, the description of the invention is divided into the following sections: (I) novel nucleic acid molecules, (II) novel proteins; and (III) applications for which the nucleic acid molecules, protein, and the substances identified using the methods described herein are suited.

I. Nucleic Acid Molecules of the Invention

The present invention provides a purified and isolated nucleic acid molecule comprising a sequence encoding a protein associated with invasion of virulent bacteria. In this respect the present invention provides a purified and isolated nucleic acid molecule comprising a sequence encoding a protein associated with invasion by Campylobacter spp. including C. jejuni and C. coli.

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

In an embodiment of the invention, an isolated nucleic acid molecule is provided having a sequence which encodes a protein having an amino acid sequence as shown in FIG. 1 or SEQ ID No.: 2.

Preferably, the purified and isolated nucleic acid molecule comprises (a) a nucleic acid sequence as shown in FIG. 1 or SEQ. ID. NO.: 1, wherein T can also be U;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (c) under stringent hybridization conditions; or (e) a nucleic acid molecule differing from any of the nucleic acids of (a) to (c) in codon sequences due to the degeneracy of the genetic code.

It will be appreciated that the invention includes nucleic acid molecules encoding truncations of proteins of the invention, and analogs and homologs of proteins of the invention and truncations thereof, as described below. It will further be appreciated that variant forms of nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequences as shown in FIG. 1 or SEQ ID NO: 1 or NO:2 and fragments thereof. The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications.

In heterologous species of C. jejuni, nucleic acid sequences having substantial homology include nucleic acid sequences having at least 30%, preferably 40–50% identity with the nucleic acid sequence as shown in FIG. 1 or SEQ ID NO.: 1. In homologous species of C. jejuni, nucleic acid sequences having substantial homology include nucleic acid sequences having at least 70%, preferably 80–90% identity with the nucleic acid sequence as shown in FIG. 1 or SEQ. ID. NO.: 1.

Another aspect of the invention provides a nucleic acid molecule, and fragments thereof having at least 15 bases, which hybridize to nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0× sodium chloride/sodium citrate (SSC) at about 45° C., followed by a wash of 2.0× SSC at 50° C. The stringency may be selected based on the conditions used in the wash step. For example, the salt concentration in the wash step can be selected from a high stringency of about 0.2× SSC at 50° C. In addition, the temperature in the wash step can be at high stringency conditions, at about 65° C.

Isolated and purified nucleic acid molecules having sequences which differ from the nucleic acid sequence shown in SEQ ID NO:1 or FIG. 1 due to degeneracy in the genetic code are also within the scope of the invention. Such nucleic acids encode functionally equivalent proteins (e.g., a CipA protein associated with invasion of C. jejuni) but differ in sequence from the above mentioned sequences due to degeneracy in the genetic code.

An isolated nucleic acid molecule of the invention which comprises DNA can be isolated by preparing a labelled nucleic acid probe based on all or part of the nucleic acid sequences as shown in FIG. 1 or SEQ. ID. NO.: 1, and using this labelled nucleic acid probe to screen an appropriate DNA library (e.g. a cDNA or genomic DNA library). For example, a whole genomic library isolated from a microorganism can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid sequence as shown in FIG. 1 or SEQ. ID. NO.: 1, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a CipA protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. A cDNA having the activity of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in the Sequence Listing as SEQ. ID. NO. 1 and in FIG. 1 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further broadly contemplates an isolated protein characterized in that it has part or all of the primary structural conformation (ie., continuous sequence of amino acid residues) of a novel protein encoded by the cipA gene of the invention. In an embodiment of the invention, an isolated protein is provided which has the amino acid sequence as shown in FIG. 1 or SEQ ID NO:2.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequence (FIG. 1 or SEQ. ID.NO:2), the protein of the present invention may also include truncations of the protein, and analogs, and homologs of the protein and truncations thereof as described herein. Truncated proteins may comprise peptides of at least fifteen amino acid residues.

Analogs of the protein having the amino acid sequence shown in FIG. 1, or SEQ.ID. NO: 2 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characterisitics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in FIG. 1, or SEQ.ID. NO:2. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention. For example, a site-specific insertional mutation is described herein which reduced the ability of *C. jejuni* to adhere to and invade a human intestinal cell line.

Deletions may consist of the removal of one or more amino acids, or discrete portions from the amino acid sequence shown in FIGS. 1 or SEQ.ID. NO:2. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in FIGS. 1, or SEQ.ID. NO:2 and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of a protein of the invention will have the same regions which are characteristic of the protein.

In heterologous species of *C. jejuni,* a homologous protein includes a protein with an amino acid sequence having at least 30%, preferably 40–50% identity with the amino acid sequence as shown in FIG. 1 or SEQ. ID. NO.: 2. In homologous species of *C. jejuni,* a homologous protein includes a protein with an amino acid sequence having at least 70%, preferably 80–90% identity with the amino acid sequence as shown in FIG. 1 or SEQ. ID. NO.: 2.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, nucleic acid molecules of the present invention having a sequence which encodes a protein of the invention may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown in FIG. 1 or SEQ. ID. NO.: 1. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

III. Applications
Detection of Nucleic Acid Molecules, Antibodies, and Diagnostic Applications Nucleic acid molecules of the invention, allow those skilled in the art to construct nucleotide probes for use in the detection of nucleotide sequences in a sample. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

The nucleotide probes thus prepared may be used to detect genes that encode proteins that are the same as, related to or analogous to CipA proteins of the invention.

Accordingly, the present invention also relates to a method of detecting the presence of nucleic acid molecules encoding a CipA protein of the invention in a sample comprising contacting the sample under hybridization conditions with one or more nucleotide probes which hybridize to the nucleic acid molecules and are labelled with a detectable marker, and, determining the degree of hybridization between the nucleic acid molecule in the sample and the nucleotide probe(s).

In an embodiment of the invention, a method is provided for detecting *C. jejuni* in a sample comprising contacting the sample with a nucleic acid molecule containing a nucleic acid sequence encoding a CipA protein, or a fragment thereof, under conditions which permit the nucleic acid molecule to hybridize with a complementary sequence in the sample to form a hybridization product, and assaying for the hybridization product.

Hybridization conditions which may be used in methods of the invention are known in the art and are described for example in Sambrook J. Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

A nucleic acid molecule of the invention also permits the identification and isolation, or synthesis of nucleotide sequences which may be used as primers to amplify a nucleic acid molecule of the invention, for example, in a polymerase chain reaction (PCR) which is discussed in more detail below. The primers may be used to amplify the genomic DNA of other bacterial species. The PCR amplified sequences can be examined to determine the relationship between the various cipA genes.

The length and bases of primers for use in a PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides, i.e., molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al. Nucl. Acid Res 4:2157, 1977) or automated techniques (See for example, Conolly, B.A. Nucleic Acids Res. 15:15 (7): 3131, 1987). The primers are capable of acting as a point of initiation of synthesis when placed under conditions which permit the synthesis of a primer extension product which is complementary to a DNA sequence of the invention, i.e., in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding a protein of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

Polymerase chain reaction as used herein refers to a process for amplifying a target nucleic acid sequence as generally described in Innis et al, Academic Press, 1990 in Mullis el al., U.S. Pat. No. 4,863,195 and Mullis, U.S. Pat. No. 4,683,202. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp3–12, Academic Press 1989.

The amplified products can be isolated and distinguished based on their respective sizes using techniques known in the art. For example, after amplification, a DNA sample can be separated on an agarose gel and visualized, after staining with ethidium bromide, under ultra violet (uv) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

Conditions which may be employed in the methods of the invention using PCR are those which permit hybridization and amplification reactions to proceed in the presence of DNA in a sample and appropriate complementary hybridization primers. Conditions suitable for a polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989. To amplify DNA template strands, preferably, the PCR utilizes polymerase obtained from the thermophilic bacterium *Thermus aquatics* (Taq polymerase, GeneAmp Kit, Perkin Elmer Cetus) or other thermostable polymerase.

It will be appreciated that other techniques such as the Ligase Chain Reaction (LCR) and NASBA may be used to amplify a nucleic acid molecule of the invention (Barney in "PCR Methods and Applications", August 1991, Vol.1(1), page 5, and European Published Application No. 0320308, published Jun. 14, 1989, and U.S. Ser. No. 5,130,238 to Malek).

A CipA protein of the invention can be used to prepare antibodies specific for the protein. Antibodies can be prepared which bind a distinct epitope in an unconserved region of the protein. An unconserved region of the protein is one which does not have substantial sequence homology to other proteins. Alternatively, a region from a well-characterized domain can be used to prepare an antibody to a conserved region of a protein of the invention. Antibodies having specificity for a protein of the invention may also be raised from fusion proteins.

Conventional methods can be used to prepare the antibodies. For example, by using a peptide of a protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77–96); and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982); and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments reactive against a protein of the invention may also be generated by screening expression libraries encoding immunoglobulin genes, or portions thereof, expressed in bacteria with peptides produced from nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)).

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, 1-123, I-125, 1-131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

Antibodies reactive against CipA proteins of the invention (e.g., enzyme conjugates or labeled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g., ELISA), immunofluorescence, immunoprecipitation, latex agglutination, hemagglutination, and histochemical tests. Thus, the antibodies may be used to identify or quantify the amount of a protein of the invention in a sample in order to diagnose C. jejuni infections.

A sample may be tested for the presence or absence of a pathogenic C. jejuni serotype by contacting the sample with an antibody specific for an epitope of a CipA protein which antibody is capable of being detected after it becomes bound to a CipA protein in the sample, and assaying for antibody bound to a CipA protein in the sample, or unreacted antibody.

In a method of the invention a predetermined amount of a sample or concentrated sample is mixed with antibody or labelled antibody. The amount of antibody used in the method is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of a pathogenic serotype can be determined by measuring the amount of labelled antibody bound to a protein of the invention in the sample or of the unreacted labelled antibody. The appropriate method of measuring the labelled material is dependent upon the labelling agent.

When unlabelled antibody is used in a method of the invention, the presence of a pathogenic *C. jejuni* serotype can be determined by measuring the amount of antibody bound to the *C. jejuni* serotype using substances that interact specifically with the antibody to cause agglutination or precipitation. In particular, labelled antibody against an antibody specific for a protein of the invention, can be added to the reaction mixture. The presence of a pathogenic *C. jejuni* serotype can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

Reagents suitable for applying the methods of the invention may be packaged into convenient kits providing the necessary materials, packaged into suitable containers. Such kits may include all the reagents required to detect a pathogenic *C. jejuni* serotype in a sample by means of the methods described herein, and optionally suitable supports useful in performing the methods of the invention.

In one embodiment of the invention the kit contains a nucleotide probe which hybridizes with a nucleic acid molecule of the invention, reagents required for hybridization of the nucleotide probe with the nucleic acid molecule, and directions for its use. In another embodiment of the invention the kit includes antibodies of the invention and reagents required for binding of the antibody to a protein specific for an pathogenic *C. jejuni* serotype in a sample. In still another embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences.

The methods and kits of the present invention have many practical applications. For example, the methods and kits of the present invention may be used to detect a pathogenic *C.*

*jejuni* serotype in any medical or veterinary sample suspected of containing *C. jejuni*. Samples which may be tested include bodily materials such as blood, urine, serum, tears, saliva, feces, tissues and the like. In addition to human samples, samples may be taken from mammals such as non-human primates, etc. Further, water and food samples and other environmental samples and industrial wastes may be tested.

Before testing a sample in accordance with the methods described herein, the sample may be concentrated using techniques known in the art, such as centrifugation and filtration. For hybridization and/or PCR-based methods described herein, nucleic acids may be extracted from cell extracts of the test sample using techniques known in the art.

Substances that Affect Adherence and/or Invasion of *C. jejuni*

A CipA protein of the invention may also be used to assay for a substance which affects adherence and/or invasion of viralent bacteria including *C. jejuni*. Accordingly, the invention provides a method for assaying for a substance that affects adherence and/or invasion of virulent bacteria including *C. jejuni* comprising mixing a protein of the invention with a test substance which is suspected of affecting the expression or activity of the protein, and determining the effect of the substance by comparing to a control.

Reagents suitable for applying methods of the invention to identify substances that affect adherence and/or invasion of virulent bacteria including *C. jejuni* may be packaged into convenient kits providing the necessary materials packaged into suitable containers. The kits may also include suitable supports useful in performing the methods of the invention.

Pharmaceutical Compositions and Methods of Treatment

Substances which affect adherence and/or invasion of virulent bacteria including *C. jejuni,* also referred to herein as active substances, identified by the methods described herein, including antisense nucleic acid molecules, and antibodies, may be used for reducing adherence and/or invasion of such bacteria and accordingly may be used in the treatment of infectious diseases caused by them.

Substances identified using the methods described herein and antibodies may be formulated into pharmaceutical compositions for adminstration to subjects in a biologically compatible form suitable for administration in vivo. As used herein "biologically compatible form suitable for administration in vivo" means a form of the substance to be administered in which therapeutic effects outweigh any toxic effects. The substances may be administered to living organisms including humans, and animals. Administration of a therapeutically active amount of pharmaceutical compositions of the present invention is defined as an amount at the pharamceutical composition, at dosages and for periods of time necessary to achieve the desired result. For example, a therapeutically active amount of a substance may vary according to factors such as disease state, age, sex, and weight of the recipient, and the ability of the substance to elicit a desired response in the recipient. Dosage regima may be adjusted to provide an optimum therapeutic response. For example, several divided doses may be administered daily or the dose may be proportionally reduced as indicated by the exigencies of the therapeutic situation.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant molecules comprising an antisense sequence or oligonucleotide fragment thereof, may be directly introduced into cells or tissues in vivo using delivery vehicles known in the art such as retroviral vectors, adenoviral vectors and DNA virus vectors. They may also be introduced into cells in vivo using physical techniques known in the art such as microinjection and electroporation or chemical methods such as coprecipitation and incorporation of DNA into liposomes. Recombinant molecules may also be delivered in the form of an aerosol or by lavage.

The utility of the substances, antibodies, antisense nucleic acid molecules, and compositions of the invention may be confirmed in animal experimental model systems.

Vaccines

The present invention relates to a vaccine against an infectious disease caused by virulent bacteria whose adherence and/or invasion is affected by a CipA protein comprising an amount of a CipA protein which is effective to provide protection against the virulent bacteria.

In one embodiment, a vaccine is provided against infectious disease caused by *C. jejuni* comprising an amount of a CipA protein which is effective to provide protection against *C. jejuni*. An example of such a vaccine is a carrier strain of having an amount of a CipA protein associated with its surface which is effective to provide protection against *C. jejuni*.

According to another embodiment, a vaccine against infectious disease caused by *C. coli* is provided. Said vaccine comprises an amount of CipA protein which is effective to provide protection against *C. coli*. An example of such a vaccine is a carrier strain having an amount of CipA protein associated with its surface which is effective to provide protection against *C. coli*.

"Infectious disease" refers to any disease or condition due to the action of virulent bacteria, including *C. jejuni*. The vaccines may be used for the prophylaxis or active immunization and treatment of infectious diseases caused by *C. jejuni*.

The carrier strain may selected so that it is incapable of multiplying in vivo. Carrier strains are obtained through selection of variants which occur naturally, or using conventional means known to those skilled in the art. Examples of suitable carrier strains are Shigella species, Salmonella species, *S. typhimurium,* Vibrio species, and Escherichia species.

The invention also relates to a method of preparing a vaccine against an infectious disease caused by a viralent bacterial whose adherence and/or invasion is affected by a CipA protein including *C. jejuni,* comprising associating with the cell surface of a carrier strain a CipA protein or portion thereof which is effective to provide protection against the virulent bacterial whose adherence and/or invasion is affected by a CipA protein including *C. jejuni*. A CipA protein or portion thereof may be associated with the cell surface of a carrier strain using conventional methods.

The vaccine may be a multivalent vaccine and additionally contain immunogens related to other infectious diseases in a prophylactically or therapeutically effective manner. Multivalent vaccines against infectious diseases caused by different infectious agents may contain a carrier strain having amounts of antigens associated with their surfaces which are effective to provide protection against the infectious agents.

A multivalent vaccine may comprise at least two carrier strains each having different immunogens associated with different infectious agents. A multivalent vaccine may contain a carrier strain having at least two different immunogens associated with different infectious agents. Thus, for example, a carrier strain may contain immunogens relating to *C. jejuni* and other pathogenic microorganisms.

A vaccine of the invention contains an immunologically effective amount of the carrier strain(s) with the integrated CipA protein. The optimum amounts of cells per dosage unit depends on the nature of the infection against which protection is required, the characteristics of the animals to be protected, and other factors known to persons skilled in the art.

A vaccine of the invention may comprise an immunologically acceptable carrier such as aqueous diluents, suspending aids, buffers, excipients, and one or more adjuvants known in the art. The vaccine may also contain preservatives such as sodium azide, thimersol, beta propiolactone, and binary ethyleneimine.

Vaccines of the invention can be intended for administration to animals, including mammals, avian species, and fish; preferably humans and various other mammals, including bovines, equines, and swine.

Vaccines of the invention may be administered in a convenient manner, such as intravenously, intramuscularly, subcutaneously, intraperitoneally, intranasally or orally. The dosage will depend on the nature of the infection, on the desired effect, on the chosen route of administration, and other factors known to persons skilled in the art.

A vaccine of the invention may contain nucleic acid molecule encoding a CipA protein of the invention. In such an embodiment, the CipA protein is produced in vivo in the host animal. The vaccines containing nucleic acids may be delivered using a suitable vector including retroviral vectors, adenoviral vectors and DNA virus vectors.

A vaccine prepared using the methods described herein may be tested in animal systems in vivo to confirm their efficacy in the prophylaxis or active immunization and treatment of infectious diseases caused by virulent bacteria *C. jejuni* and to determine appropriate dosages and routes of administration.

As discussed above, CipA proteins of the invention are also useful for preparing antibodies which may be used as a means of passive immunization.

The invention will be more fully understood by reference to the following examples. However, the examples are merely intended to illustrate embodiments of the invention and are not to be construed to limit the scope of the invention.

EXAMPLE

Materials and methods used in the example described herein include the following:

Materials and Methods:

Genetic methods: Isolation of DNA and total RNA, restriction enzyme digestion, gel electrophoresis, radiolabelling of DNA probes, Southern hybridization, and transformation of plasmids into *E. coli* were performed according to standard protocols (Sambrook et al., 1989). DNA was sequenced on both strands by the dideoxy chain-termination method (Sanger et al., 1977) using Sequenase version 2.0 (United States Biochemical Corporation). The transcription start site of the gene was determined by primer extension as described previously (Hong et al., 1995). Briefly, [g-32P] ATP-labelled oligonucleotide (30 ng) was mixed with 25 $\mu$g total *C. jejuni* RNA, and cDNA was synthesized using AMV reverse transcriptase (Pharmacia). The newly synthesized DNA was resolved on a 6% polyacrylamide sequencing gel alongside sequencing ladders generated using the same oligonucleotide primer.

Identification of SalI-containing library clones: Nine hundred and sixty recombinant clones from a library of *C. jejuni* TGH9011 genomic DNA constructed in pBluescriptII KS+ (Chan et al., 1995) were divided into pools of eight. Plasmid DNA in each pool was digested to completion with SalI and the products resolved in a 1% agarose gel. The vector pBluescript contains a unique SalI recognition sequence within the multiple cloning site. Therefore, the presence of more than 8 SalI-cleaved restriction bands in a given pool of recombinant plasmids indicated the presence of a SalI site within the *C. jejuni* DNA insert of one of the plasmids in that pool. Plasmids from pools with putative SalI site-containing inserts were then analyzed individually. Recombinant plasmids containing DNA from one of the three *C. jejuni* rrn operons, each of which harbors a unique SalI site (Kim et al., 1995), were excluded by Southern hybridization. Using this strategy, recombinant plasmid pE3-8 was identified as carrying a Campylobacter SalI site-containing DNA insert which was unrelated to the DNA regions encoding the rrn operons of *C. jejuni.*

Maxicell analysis of proteins: Genes carried on plasmids pE3-8 and p2E3-8 were expressed in E. coli DR1984 using a maxicell procedure (Sancar et al., 1979) described previously (Hong et al., 1995). Plasmid-encoded proteins were radiolabelled with [35S]methionine, separated on a SDS-7.5% polyacrylamide gel (Laemmli, 1970), and visualised by autoradiography.

Construction of isogenic mutant strain: An isogenic *C. jejuni* mutant harboring a disrupted orfS gene was constructed using a gene replacement strategy (Labigne-Roussel et al., 1988). Briefly, a kanamycin resistance (Kmr) cassette was inserted into a unique StuI site of p2E3-8, at nucleotide (nt) 890 of orfS (see FIG. 1). Disrupted orfS was returned to *C. jejuni*TGH9011 by natural transformation using a modification of the procedure of Wang and Taylor (1990). Briefly, *C. jejuni* TGH9011 cells were grown to mid-log to late-log phase in Mueller-Hinton (MH) broth and 0.2 ml was used to inoculate 1 ml of fresh MH medium. The culture was incubated at 37° C. under 50/0 CO2 for 6 h before plasmid DNA (0.1–0.2 mg) containing disrupted orfS was added. The culture was further incubated for 20 h, then aliquots were spread onto MH agar plates containing kanamycin at 100 mg/ml. Kanamycin resistant *C. jejuni* colonies were isolated. Southern hybridization analysis of the Kmr *C. jejuni* mutant strains verified the presence of a disrupted orfS allele due to a site-specific double cross-over event, with concomitant loss of the wild-type orfS locus.

Adherence and invasion assays: INT 407 (human embryonic intestine: ATCC CCL 6) cells grown as monolayers in Eagle's minimal essential medium (E-MEM; Gibco Life Technologies Inc.) supplemented with 15% heat-inactivated fetal calf serum (Cansera International), 1 mM glutamine, and 0.075% sodium bicarbonate were maintained in a humidified 5% C02 incubator at 37° C. *C. jejuni* cultures were grown to mid-log phase in MH broth (with or without kanamycin at 100 mg/ml), the cells were harvested and resuspended in fresh MH medium to a cell concentration of approximately $1 \times 10^9$ CFU/ml.

Bacteria adhering to and invading INT407 cells were quantified. The protocol used was modified from the method described by Yao et al. (1994). Briefly, confluent monolayers of INT 407 (approximately $1 \times 10^6$ cells) in the wells of a 24-well plate were washed three times with serum-free E-MEM and *C. jejuni* added at approximately $5 \times 10^7$ CFU/well. The actual number of input bacteria was determined by colony plate count. In contrast to the protocol of Yao et al. ( ), contact between the bacteria and INT407 cells was not assisted by centrifugation. The plate was incubated for 3 hours at 37° C. in an atmosphere of 5% CO2–95% air. Medium containing non-adherent bacteria was then removed from each well, the monolayers washed three times with E-MEM followed by the addition of fresh E-MEM with or without gentamicin at a concentration of 100 mg/ml. After a further 3 hour incubation period under the same conditions, the monolayers were washed extensively with sterile Dulbecco's PBS (Gibco Life Technologies Inc.) and INT 407 cells were released from the wells by incubation with 0.05% trypsin-EDTA. Collected intestinal cells with adherent or intracellular bacteria were placed in distilled water containing 0.1% bovine serum albumin and vortexed to lyse the tissue culture cells. A bacterial pellet recovered by centrifugation was resuspended in PBS, and the CFU enumerated. The actual number of input bacteria and those present in the final lysates were enumerated by colony plate count. All assays were performed in duplicate.

Adhesion was calculated as the percentage of input bacteria adhering after extensive washing without antibiotic treatment and invasion the percentage of adherent bacteria surviving gentamicin treatment. Results from four individual experiments run in duplicate were expressed relative to values for wild-type (*C. jejuni* TGH9011). Data are reported as means ±standard error. Differences between groups were compared using the two-tailed, unpaired Student's t test. Differences were considered significant at the level of $P<0.05$.

Pulsed-field gel electrophoresis: For PFGE, genomic DNA was prepared in agarose plugs as previously described (Bourke et al., 1995). Restriction enzyme digestion with SalI was performed in a total volume of 0.3 ml with 20–30 U of enzyme per insert and incubated overnight at 37° C. Pulsed-field gel electrophoresis was undertaken using a contour-clamped homogenous-electric field (CHEF) apparatus. DNA samples were loaded onto 1.1% agarose (ICN Biomedicals) and run in 0.5× TBE buffer at 14° C. Optimal resolution in the region of the 43 kb SalI E band was achieved using a 2 sec pulse time over the course of 24 h with a field strength of 10 V/cm. Lambda concatemers (Promega) were used as size markers. The gel was stained for 30 min in ethidium bromide (0.5 mg/ml), destained overnight and photographed under ultraviolet light.

Results:

Identification and characterization of a SalI site-containing ORF: The recombinant plasmid pE3-8 containing a 7.5 kb insert was found to contain a SalI restriction site situated approximately 1.5 kb from the 3' end of the insert. The nucleotide sequence of a 1526 bp region close to the 3' end of the pE3-8 insert showed the presence of a translational open reading frame (ORF) of 1392 nucleotides in length (FIG. 1). This ORF contained the *C. jejuni* SalI site (GTCGAC), located at nt 329–334, and was provisionally named orfS. The orfS ORF/gene encodes a protein of 464 amino acids initiated by Met at nt 100–102. The predicted molecular weight of the OrfS protein was 55,651. A 6 bp sequence, AAGAGG, located 10 nucleotides upstream from the proposed translational start codon matches 5 of the 6 nucleotides of the Shine-Dalgarno consensus sequence. Primer extension mapping showed a predicted transcription start point for orfS at an adenine residue (FIG. 2) corresponding to nt 85 (FIG. 1). Thirteen nucleotides upstream from the transcription start point is the sequence TAAATT which matches 4 of the 6 nucleotides of the consensus sequence for a Pribnow box. A further 29 nt upstream of this predicted –10 promoter region is the sequence ATGACA which matches 5 of the 6 nucleotides of the consensus sequence for a –35 promoter region (FIG. 1).

A search of the GenBank protein database using the BLAST search algorithm (Altschul et al., 1990) did not reveal any significant similarity between the predicted OrfS protein and other known protein sequences. Analysis of the OrfS deduced amino acid sequence using the pSORT algorithm (Nakai & Kanehisa, 1991) did not identify a potential signal peptide or transmembrane domains. A hydropathy plot of the orfS gene product obtained by Kyte-Doolittle analysis (1982) also did not indicate the presence of any potential transmembrane segments within the translated protein.

ClaI sites within the DNA insert of pE3-8 were mapped by partial digestion (Smith & Birnstiel, 1976) Incomplete cleavage of pE3-8 with ClaI generated a 2 kb partially-digested ClaI fragment which contained the complete 1392 bp orfS and approximately 500 bp of the 5' flanking region of this ORF. This 2 kb ClaI fragment was subcloned into pBluescript, and the newly constructed recombinant plasmid designated $p^2$E3-8.

Identification of plasmid-encoded cloned proteins: The polypeptide encoded by orfS was identified by comparing the proteins synthesized from several plasmids in maxicells. An autoradiograph of [35S]methionine-labelled proteins resolved by SDS-PAGE (FIG. 3) showed a polypeptide of 55 kDa which was likely to be the protein expressed from orfS in pE3-8 and p2E3-8 (FIG. 3, lanes 3 and 4). Proteins of 31 and 28 kDa representing the precursor and mature forms of β-lactamase, respectively, were observed in *E. coli* DR1984 cells containing pBluescript, pE3-8, and p2E3-8 (FIG. 3, lanes 2–4). These polypeptides were not found in DR1984 cells in the absence of plasmid (FIG. 3, lane 1). Cells carrying pE3-8 revealed two additional proteins of 43 kDa and 41 kDa (FIG. 3, lane 3). These gene products are presumably from *C. jejuni* ORFs upstream of orfS as they were not observed in cells containing p2E3-8 (FIG. 3, lane 4).

Construction of a *C. jejuni* orfS::Kmr mutant: To investigate the function of orfS, allelic replacement mutagenesis was performed to generate an isogenic strain of *C. jejuni* containing a disrupted orfS gene. Of the antibiotic resistant strains isolated, *C. jejuni* 901LK1 was identified having an orfS::Kmr insertion in the genome with disappearance of the wild-type orfS allele (data not shown). No noticeable difference was observed between the growth rate of *C. jejuni* 901LK1 (orfS::Kmr) compared to parental *C. jejuni*TGH9011 cells.

Comparison of *C. jejuni* wild-type and mutant strains in adherence and invasion assays: To investigate the effect of disrupting the orfS gene on the initial interactions of *C. jejuni* with host cells, the relative abilities of strains TGH9011 (wild-type control) and 901LK1 (orfS::Kmr) to attach to and invade INT407 cells was compared. Percent adherence and %invasion for the control strain TGH9011 was 3.4% of input bacteria and 1.3% of adherent bacteria, respectively. Adherence of *C. jejuni* 901LK1 to INT407 cells was significantly less than wild-type (42.5±10.5% relative to wild-type control; P <0.002). Moreover, the mutant *C. jejuni* strain containing orfS::Kmr exhibited reduced ability to invade INT407 cells (47.5±7.7% relative to wild-type; P<0.0005). As insertional mutagenesis of orfS diminished the ability of *C. jejuni* to attach to and enter INT407 cells, the SalI site-containing non-rRNA gene provisionally named orfS was designated cipA (Campylobacter invasion phenotype).

Figure 4:
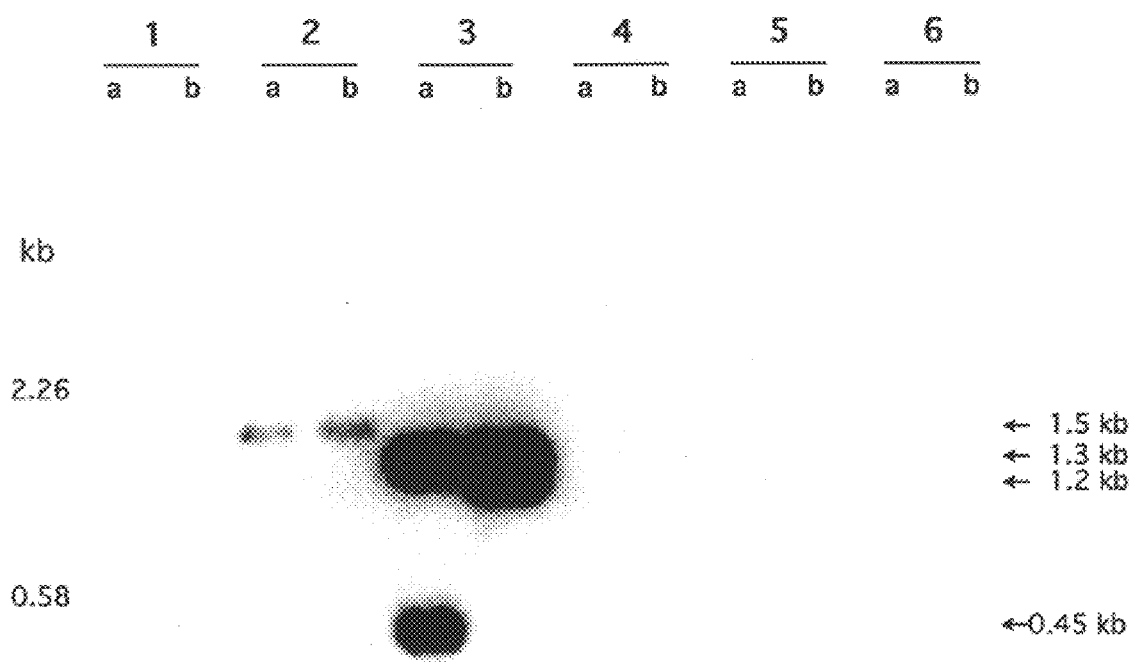
FIG. 4 shows Southern blot analysis of genomic DNA from representative samples of various Campylobacteraceae.

Identification of cipA in other species: To determine whether the cipA gene characterized in this study is conserved among related organisms, DNA from multiple isolates of *C. jejuni, C. lari, C. coli, C. upsaliensis, C. sputorum*, and *Arcobacter nitrofigilis* were completely digested with ClaI, or ClaI and SalI together, and transferred onto a nylon membrane. The 1.2 kb EcoRI-SalI fragment of the cipA gene was used to probe this blot. Under low stringency hybridization conditions, only the *C. coli* DNA showed cross-hybridization to the *C. jejuni* cipA probe (FIG. 4, lane 2). The probe hybridized with two *C. jejuni* ClaI bands and three bands of the ClaI/SalI double digest, as predicted from the cipA sequence (FIG. 1). This hybridization pattern was conserved in four different *C. jejuni* isolates studied (data not shown). The homologous cipA gene in *C. coli* does not have a ClaI or SalI site as only one hybridizing band was observed in ClaI and ClaI/SalI digests (FIG. 4, lanes 2a and 2b).

Figure 5A:
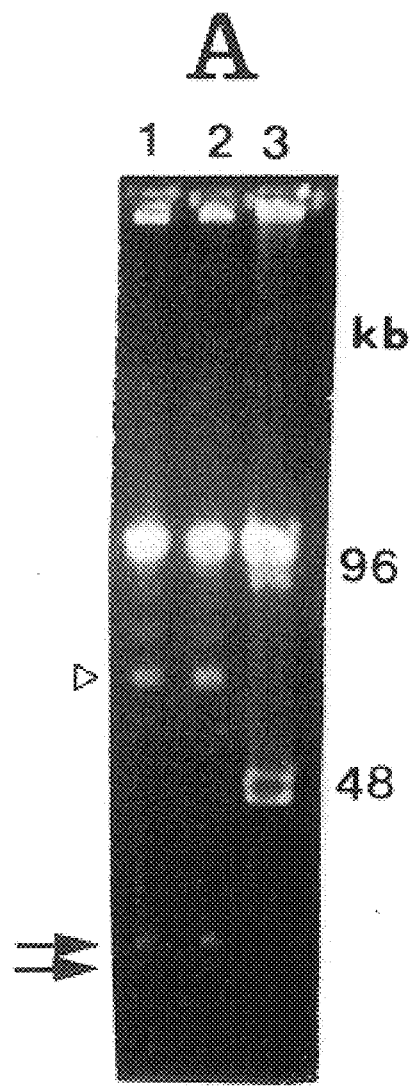
FIG. 5A is a gel showing the resolution of C. jejuni SalI-E and SalI-F fragments using pulsed-field gel electrophoresis.
Figure 5B:
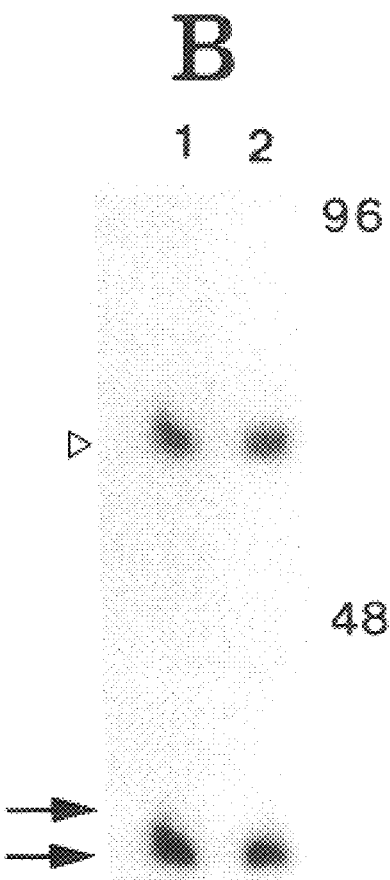
FIG. 5B is a Southern blot of the gel shown in FIG. 5A probed with plasmid pE3-8 indicating the contiguity of SalI-F and SalI-D on the physical map of C. jejuni TGH9011.
Figure 5C:
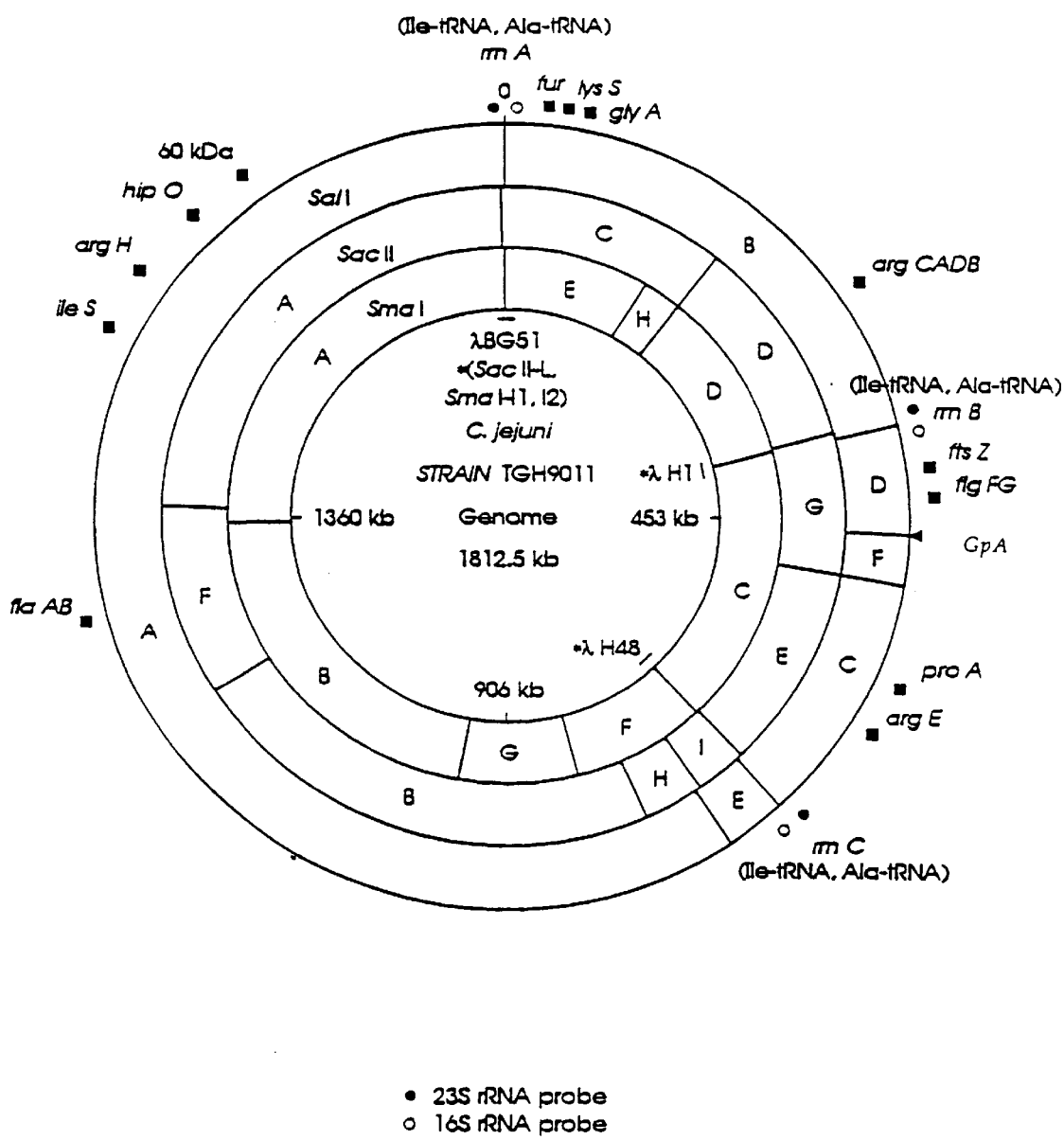
FIG. 5C is an updated physical map of C. jejuni TGH9011 showing the position of the newly recognized SalI-F fragment.

Localization of cipA to the physical map of *C. jejuni*: The SalI site in the cipA gene was mapped using pulsed-field gel electrophoresis and Southern hybridization (FIG. 5). Plasmid pE3-8 was used to probe a blot of the PFGE gel shown in FIG. 5A. The result, shown in FIG. 5B, indicates that pE3-8 acts as a linking clone for the SalI D fragment and the smaller of the two doublet bands, designated SalI F. Therefore, SalI F is positioned adjacent to SalI D in a clockwise direction on the physical map of *C. jejuni* (FIG. 5C).

Growth of *C. jejuni* strains TGH9011 (parent) and 901LK1(cipA::Kmr) were comparable, suggesting that cipA is a non-essential gene for growth of this organism in a laboratory culture medium. Many pathogens elaborate virulence determinants, eg. adhesins and invasins, which may not be utilized by the organism under routine laboratory growth conditions. Therefore whether the disruption of the cipA gene altered the ability of *C. jejuni* to interact with host cells was investigated. Pathogen-host cell interactions are crucial for bacterial survival within a host environment, moreover, studies of several pathogens have demonstrated that some virulence genes are specifically triggered by contact of the organism with eukaryotic cells (Rosqvist, Sory, Watarai, Zierler). Adherence and invasion assays using intestinal INT407 cells are widely used to investigate the pathogenic capability of *C. jejuni* (Yao, 1994; Wassenaar, 1994; Grant, 1993; Pesci, 1994). To determine if cipA was involved in binding and internalization of *C. jejuni* into host cells, the relative abilities of strains TGH9011 (wild-type control) and 901LK1(orfS::Kmr) to adhere to and invade INT407 cells were compared. Insertional disruption of the cipA gene resulted in a 43% decrease in *C. jejuni* cells attaching to INT407 cells. Of the adherent bacteria, there was a marked reduction in the number subsequently invading organisms. Under the conditions of our assay procedure, the values expressed for adherent bacteria refer to those organisms bound to the surface of INT407 cells as well as to those which were previously bound and are now internalized. The values for invasion, defined as the percentage of adherent bacteria surviving gentamicin treatment, refer only to internalized organisms. Analysis of wild-type *C. jejuni* TGH9011 revealed that only 1.3% of adherent bacteria actually entered host cells. Despite this low level of invasiveness, it was clear from multiple experiments that insertional mutagenesis of the cipA gene consistently resulted in a decrease in *C. jejuni* internalization. Bacterial attachment also appeared to be diminished by disruption of cipA. On the basis of the results from this study where both %adherence and %invasion were reduced by approximately 45%, although only 1.3% of adherent TGH9011 are invasive, it would appear that disruption of cipA affects independently the *C. jejuni* attachment and internalization mechanisms.

Failure to identify a potential N-terminal signal sequence in CipA indicates that the protein is probably localized to the cytoplasm, where it may play a regulatory role in expression or secretion of specific adherence and invasion proteins (effector proteins) of *C. jejuni*. Alternatively, CipA itself may be an effector molecule secreted out of the cell via a type III secretion system upon host cell contact. Several enteropathogens, such as Yersinia spp., Salmonella spp., Shigella spp., and enteropathogenic *Escherichia coli*, have been shown to utilize type III secretion to deliver invasins, which lack signal peptides, into host cells (Mecsas, 1996). Whether CipA is an effector protein, a regulatory protein, or a chaperone for secretion of effector molecules, is yet to be determined.

Attachment and invasion of *C. jejuni* to INT407 cells was reduced, but not totally abolished by disruption of the cipA gene. This suggests that CipA may play a role in pathogenesis, but that other factors with a similar function may also contribute to *C. jejuni* virulence. Compatible with this idea is the finding that the cipA gene is not highly conserved among other enterovirulent Campylobacters. However, it is noteworthy that both of the important human enteropathogens of this genus, *C. jejuni* and *C. coli* (Ketley, 1995) harbor the cipA gene. Expression of the cipA gene product may significantly enhance the virulence of *C. jejuni*, and the presence of a rare SalI site in the cipA sequence of all *C. jejuni* strains studied supports the concept that cipA may confer an evolutionary advantage for this enteric pathogen.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

Below full citations are set out for the references referred to in the specification and detailed legends for the figures are provided.

The application contains sequence listings which form part of the application.

REFERENCES

Altschul, S. F., W. Gish, M. Miller, E. W. Myers, and D. J. Lipman. 1990. Basic local alignment search tool. J. Mol. Biol. 215:403–410.

Bourke, B., P. Sherman, H. Louie, E. Hani, P. Islur, and V. L. Chan. 1995. Physical and genetic map of the genome of Campylobacter upsaliensis. Microbiol. (UK) 141:2417–2424.

Chan, V. L., H. Louie, and H. L. Bingham. 1995. Cloning and transcription regulation of the ferric uptake regulatory gene of *Campylobacter jejuni* TGH9011. Gene 164:25–31.

Chang, N., and D. E. Taylor. 1990. Use of pulsed-field agarose gel electrophoresis to size genomes of Campylobacter species and to construct a SalI map of *Campylobacter jejuni* UA580. J. Bacteriol. 172:5211–5217.

Grant, C. C. R., M. E. Konkel, W. Cieplak, Jr., and L. S. Tomkins. 1993. Role of flagella in adherence, internalization, and translocation of *Campylobacter jejuni* in nonpolarized and polarized epithelial cell cultures. Infect. Immun. 61:1764–1771.

Hani, E. K., and V. L. Chan. 1995. Expression and characterization of *Campylobacter jejuni* benzoylglycine amidohydrolase (hippuricase) gene in *Escherichia coli*. J. Bacteriol. 177:2396–2402.

Hong, Y., T. Wong, B. Bourke, and V. L. Chan. 1995. An isoleucyl-tRNA synthetase gene from *Campylobacter jejuni*. Microbiol. (UK) 141:2561–2567.

Ketley, J. M. 1995. Virulence of Campylobacter species: a molecular genetic approach. J. Med. Microbiol. 42:312–327.

Kim, N. W., R. R. Gutell, and V. L. Chan. 1995. Complete sequences and organization of the rrnA operon from *Campylobacter jejuni* TGH9011 (ATCC43431). Gene 164:101–106.

Kim, N. W., R. Lombardi, H. Bingham, E. Hani, H. Louie, D. Ng, and V. L. Chan. 1993. Fine mapping of the three rRNA operons on the updated genomic map of *Campylobacter jejuni* TGH9011 (ATCC43431). J. Bacteriol. 175:7468–7470.

Kim, N. W., H. Bingham, R. Khawaja, H. Louie, E. Hani, K. Neote, and V. L. Chan. 1992. Physical map of *Campylobacter jejuni* TGH9011 and localization of 10 genetic markers by use of pulsed-field gel electrophoresis. J. Bacteriol. 174:3494–3498.

Kyte, J., and R. F. Dolittle. 1982. A simple method for displaying the hydropathic character of a protein. J. Mol. Biol. 157:105–132.

Labigne-Roussel, A., P. Courcoux, and L. Tompkins. 1988. Gene disruption and replacement as a feasible approach for mutagenesis of *Campylobacter jejuni*. J. Bacteriol. 170:1704–1708.

Laemmli, U. K. 1970. Cleavage of structural proteins during the assembly of the head of bacteriophage T4. Nature 227:680–685.

McClelland, H., R. Jones, Y. Patel, and M. Nelson. 1987. Restriction endonucleases for pulsed-field mapping of bacterial genomes. Nucl. Acids Res. 15:5985–6005.

Mecsas, J., and E. J. Strauss. 1996. Molecular mechanisms of bacterial virulence: type III secretion and pathogenicity islands. Emerg. Infect. Dis. 2:271–288.

Nakai, K., and M. Kanehisa. 1991. Expert system for predicting protein localization sites in Gram-negative bacteria. Proteins: Structure, Function and Genetics 11:95–110.

Rosqvist, R., K. E. Magnusson, and H. Wolf-Watz. 1994. Target cell contact triggers expression and polarized transfer of Yersinia YopE cytotoxin into mammalian cells. EMBO J. 13:964–972.

Sambrook, J., E. F. Fritsch, and T. Maniatis. 1989. Molecular cloning: a laboratory manual, vol. 1, 2, and 3. Cold Spring Harbor Laboratory Press, Cold Spring Harbor, N.Y.

Sancar, A., A. M. Hack, and W. D. Rupp. 1979. Simple method for identification of plasmid-coded proteins. J. Bacteriol. 137:692–693.

Sanger, F., S. Nicklen, and S. Coulson. 1977. DNA sequencing with chain-terminating inhibitors. Proc. Natl. Acad. Sci. USA 74:5463–5467.

Smith, H. O., and M. L. Birnstiel. 1976. A simple method for DNA restriction site mapping. Nucl. Acids Res. 3:2387–2399.

Sory, M. P., and G. R. Cornelis. 1994. Translocation of a hybrid YopE-adenylate cyclase for Yersinia enterolitica into HeLa cells. Mol. Microbiol. 14:583–594.

Yao, R., D. H. Burr, P. Doig, T. J. Trust, H. Niu, and P. Guerry. 1994. Isolation of motile and non-motile insertional mutants of Campyloabcter jejuni: the role of motility in adherence and invasion of eukaryotic cells. Mol. Microbiol. 14:883–893.

Wang, Y., and D. E. Taylor. 1990. Natural transformation in Campylobacter species. J. Bacteriol. 172:949–955.

Wassenaar, T. M., N. M. C. Bleumink-Pluym, D. G. Newell, P. J. M. Nuijten, and B. A. M. van der Zeijst. 1994. Differential flagellin expression in a flaA flaB+mutant of *Campylobacter jejuni*. Infect. Immun. 62:3901–3906.

Watarai, M., T. Tobe, M. Yoshikawa, and C. Sasakawa. 1995. Contact of Shigella with host cells triggers release of Ipa invasins and is an essential function of invasiveness. EMBO J. 14:2461–2470.

Zierler, M. K., and J. E. Galan. 1995. Contact with cultured epithelial cells stimulates secretion of *Salmonella typhimurium* invasion protein InvJ. Infect. Immun. 63:4024–4028.

DETAILED FIGURE LEGENDS

FIG. 1, Sequence of the orfS (cipA) gene and its flanking regions obtained from *C. jejuni* genomic DNA library clone E3-8. The deduced amino acid sequence is indicated in single letter code below the nucleotide sequence. The SalI restriction site is under- and overlined. The potential Shine-Dalgarno sequence (SD), Pribnow box (PB) and −35 consensus regions are underlined and the transcription start site, residue A (located at nucleotide 85) is indicated by a solid arrowhead.

FIG. 2, Primer extension mapping of the transcription start site of the orfS (cipA) mRNA. Lane E shows the primer extension products of *C. jejuni*RNA catalyzed by AMV reverse transcriptase. Lanes G, A, T, C are the dideoxy-chain termination sequencing reaction products generated using the same primer with the complete promoter region. The nucleotide corresponding to the transcription start site is indicated with an asterisk.

FIG. 3, Maxicell analysis for the elucidation of the plasmid-encoded proteins. The [35S]methionine-labelled proteins were resolved in a 7.5% SDS-PA gel; lane 1, DR1984 with no plasmid; Lane 2, DR1984 with pBluescript; lane 3, DR1984 with pE3-8 and lane 4, DR1984 with p2E3-8. The molecular weight standards are marked in kilodaltons.

FIG. 4, Southern blot analysis of genomic DNA from representative samples of various Campylobacteraceae. *C. lari* (lane 1), *C. coli* (lane 2), *C. jejuni* TGH9011 (lane 3), Arcobacter nitrofigilis (lane 4), C. upsalensis (lane 5) and *C. sputorum* (lane 6) digested with ClaI and SalI (a), or ClaI (b).

Equivalent amounts of DNA were loaded in each well. The fragments were separated in a 0.4% agarose gel, transferred to GeneScreen Plus nylon membrane (Dupont-NEN) and probed with a radiolabelled 1.2 kb EcoRI-SalI fragment from pE3-8. The filter was washed with 2× SSC at room temperature for 5 min before being exposed to X-Ray film.

FIG. 5A. Resolution of *C. jejuni* SalI-E and SalI-F fragments using pulsed-field gel electrophoresis. A 1.1% gel was run for 24 hours using a 2 second pulse time in a field strength of 10V/cm. Lanes 1 and 2 depict SalI-digested *C. jejuni* DNA. Only the SalI-D (open triangle), SalI-E (upper arrow), and SalI-F (lower arrow) fragmets are resolved using this pulse time. Lambda concatemers were used as size markers (lane 3). Molecular sizes are indicated to the right of the gel.

FIG. 5B. Southern blot of gel shown in FIG. 5A probed with plasmid pE3-8 indicating the contiguity of SalI-F and SalI-D on the physical map of *C. jejuni* TGH9011.

FIG. 5C. The updated physical map of *C. jejuni* TGH9011 showing the position of the newly recognized SalI-F fragment.

We claim:

1. A purified and isolated nucleic acid molecule encoding a protein associated with adherence and invasion of *Campylobacter jejuni* and having a nucleic acid sequence which comprises: (a) a nucleic acid sequence as shown in SEQ ID NO:1 wherein T can also be U; or (b) nucleic acid sequences complementary to (a).

2. A recombinant molecule adapted for transformation of a host cell comprising a nucleic acid molecule as claimed in claim 1 and an expression control sequence operatively linked to the DNA segment.

3. A transformed host cell including the recombinant molecule as claimed in claim 2.

4. A method for preparing a Campylobacter invasion phenotype (CipA) protein associated with adherence and invasion of *C. jejuni* comprising culturing a host cell according to claim 3 under conditions which allow the expression of the protein and isolating the expressed protein.

* * * * *

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 1522 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 98..1492

(xi) SEQUENCE DESCRIPTION: SEQ ID NO:1:

CTTTAATTAA AGTTTATTTT TGATAATATA TTTAAATTTC ATGACATTTA AATATTTATG        60

AATTATATAT AAATTAAATA CAATTAAAAG AGGTTAT ATG CAA AAT CTT TTA CTC       115
                                        Met Gln Asn Leu Leu Leu
                                          1               5

TAT ATA AAA AAT AAC CTA ACT CCA ACC CTA GCT CAA ATT CTT TTA CAA        163
Tyr Ile Lys Asn Asn Leu Thr Pro Thr Leu Ala Gln Ile Leu Leu Gln
         10                  15                  20

GCT TTA AAA AAT TCG AAT AAT GAA AAA TTT TTT ACC TTT GTT TTG AAA        211
Ala Leu Lys Asn Ser Asn Asn Glu Lys Phe Phe Thr Phe Val Leu Lys
     25                  30                  35

AAT ATT GAA ACA ATT TGC ACT TGG CTC AAT TCT AAC GAA TTT AGG GAT        259
Asn Ile Glu Thr Ile Cys Thr Trp Leu Asn Ser Asn Glu Phe Arg Asp
 40                  45                  50

AGA TAT TTA TCA ACA AAA CAT CCT TAT CCA CCT TTA ATC AAT CCT AAT        307
Arg Tyr Leu Ser Thr Lys His Pro Tyr Pro Pro Leu Ile Asn Pro Asn
 55                  60                  65                  70

TTT ATA GAA ATA GAT TCT AGT CGA CAT TGC GCA GAA TTA GCT TGG GAT        355
Phe Ile Glu Ile Asp Ser Ser Arg His Cys Ala Glu Leu Ala Trp Asp
                 75                  80                  85

TTA AAT TTA CCC CTA CCT AAA CAC TAT AAA TTT ATC TAT ATT TCT CCA        403
Leu Asn Leu Pro Leu Pro Lys His Tyr Lys Phe Ile Tyr Ile Ser Pro
             90                  95                 100

CAT GGC GTT GGA GCA GCA GCA TTT TTA AGA TAC CTT AAT CAA TGT TGC        451
His Gly Val Gly Ala Ala Ala Phe Leu Arg Tyr Leu Asn Gln Cys Cys
         105                 110                 115

GAT GTA ACT TGT TTT GCC TCC TGG GTT TTA CCA CCT GAT AGC AAA GAG        499
Asp Val Thr Cys Phe Ala Ser Trp Val Leu Pro Pro Asp Ser Lys Glu
     120                 125                 130

AGA TAT TGT ATT AAT TAC ATG TGT CTA AAT GAT AAT ACA ATT GCT CAA        547
Arg Tyr Cys Ile Asn Tyr Met Cys Leu Asn Asp Asn Thr Ile Ala Gln
135                 140                 145                 150

TAT GCT ATT AAT ATA TCA GAA ATT AAT CTA CCT TAT TTT GAT AAA TAT        595
Tyr Ala Ile Asn Ile Ser Glu Ile Asn Leu Pro Tyr Phe Asp Lys Tyr
                155                 160                 165
```

-continued

```
CTA TCT TTA TTA GAT TTT AAT TCT AAG ATT ATT TGC GGA GTT CGA GAT       643
Leu Ser Leu Leu Asp Phe Asn Ser Lys Ile Ile Cys Gly Val Arg Asp
        170                 175                 180

CCA ATA GGA CTT TTA AAG CAT AGC TGG GGA AGA GAT TGG AGT AAA GTT       691
Pro Ile Gly Leu Leu Lys His Ser Trp Gly Arg Asp Trp Ser Lys Val
        185                 190                 195

TTA AGA AAC TAT CCC CCT GAA TTT AAT CTA ACT TAT GAT TGG CGT TAT       739
Leu Arg Asn Tyr Pro Pro Glu Phe Asn Leu Thr Tyr Asp Trp Arg Tyr
200                 205                 210

TAC ATC AAC TAT CTT ACT CAT CAA AAT CAT AAA ATT AAA ATC GAT ATA       787
Tyr Ile Asn Tyr Leu Thr His Gln Asn His Lys Ile Lys Ile Asp Ile
215                 220                 225                 230

AAT GAA CTA CAA CAA GGA GTT TTT ATC ATC TCT TAT TTA TTA AAA TAT       835
Asn Glu Leu Gln Gln Gly Val Phe Ile Ile Ser Tyr Leu Leu Lys Tyr
            235                 240                 245

TTT AAC AAA GAC AAT GTA TAC TAT CTT GAT ATG GAA GAA ATC CGC CAA       883
Phe Asn Lys Asp Asn Val Tyr Tyr Leu Asp Met Glu Glu Ile Arg Gln
            250                 255                 260

TCA AAG GCC TTC GAT ACC ATG AAT TTA CTT GCT ATA AAT TTT AAT TTT       931
Ser Lys Ala Phe Asp Thr Met Asn Leu Leu Ala Ile Asn Phe Asn Phe
            265                 270                 275

ACC CCC CCC CAT AAA GAT AAA TTA GAT TTA TTT AAA ATT AAA GAA TTT       979
Thr Pro Pro His Lys Asp Lys Leu Asp Leu Phe Lys Ile Lys Glu Phe
280                 285                 290

AGA GGT TAT ATT CGC TAT CTT TTT CCT ATT ACA CTT TAT GCA AAT TCT      1027
Arg Gly Tyr Ile Arg Tyr Leu Phe Pro Ile Thr Leu Tyr Ala Asn Ser
295                 300                 305                 310

AAA GAT ATT AAT AAC ACC TTT TAT CTT AAT ACT CCT AAA AAT AAT AAA      1075
Lys Asp Ile Asn Asn Thr Phe Tyr Leu Asn Thr Pro Lys Asn Asn Lys
            315                 320                 325

AAT TTC AAT ATT GAT AGA ACT TCT AGC ATT CCC ATA ATT TTA GAC AGA      1123
Asn Phe Asn Ile Asp Arg Thr Ser Ser Ile Pro Ile Ile Leu Asp Arg
            330                 335                 340

AAA CAT ATC AAT CAT GAA AAA ATA GAC ATA ATA CAA GAA ATT ATA AAA      1171
Lys His Ile Asn His Glu Lys Ile Asp Ile Ile Gln Glu Ile Ile Lys
            345                 350                 355

AAC GAC CTA TGT AAT GAT ATG GGT GTA TAT ATT GAT AAA AAT GAT TTT      1219
Asn Asp Leu Cys Asn Asp Met Gly Val Tyr Ile Asp Lys Asn Asp Phe
360                 365                 370

AAG CAA TTA GAA CAA AAC AAT CTT TTA TTT TCA ACA ATT AAA CAT TAT      1267
Lys Gln Leu Glu Gln Asn Asn Leu Leu Phe Ser Thr Ile Lys His Tyr
375                 380                 385                 390

TTG TAT GAT TTT TTA TAT CAA ATT AAA ATA ACC ATA GAT GAA ACA GAA      1315
Leu Tyr Asp Phe Leu Tyr Gln Ile Lys Ile Thr Ile Asp Glu Thr Glu
            395                 400                 405

TCA AAA ATG ATG AAA GAA AAA GAT GTA ATA GAT TAT TTT ATA AAA AAT      1363
Ser Lys Met Met Lys Glu Lys Asp Val Ile Asp Tyr Phe Ile Lys Asn
            410                 415                 420

AAA TCA CTT ATT TAC ACT TTT TTT AAT ATT TTT GAA AAT GAA CTA AAT      1411
Lys Ser Leu Ile Tyr Thr Phe Phe Asn Ile Phe Glu Asn Glu Leu Asn
            425                 430                 435

CAT TTA AAA CAA ACA CAT CCT CAT ATT ATT GAT TCT TGG AAA TAT TAT      1459
His Leu Lys Gln Thr His Pro His Ile Ile Asp Ser Trp Lys Tyr Tyr
440                 445                 450

AAA GAA TTT GAA AAA ATA TAC AAA GAT AAA TAA TCATATCACT TACACAAAAT    1512
Lys Glu Phe Glu Lys Ile Tyr Lys Asp Lys
455                 460

CAATAGGATC                                                           1522
```

(2) INFORMATION FOR SEQ ID NO:2:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Asn Leu Leu Tyr Ile Lys Asn Asn Leu Thr Pro Thr Leu
 1               5                  10                  15

Ala Gln Ile Leu Leu Gln Ala Leu Lys Asn Ser Asn Asn Glu Lys Phe
                20                  25                  30

Phe Thr Phe Val Leu Lys Asn Ile Glu Thr Ile Cys Thr Trp Leu Asn
         35                  40                  45

Ser Asn Glu Phe Arg Asp Arg Tyr Leu Ser Thr Lys His Pro Tyr Pro
     50                  55                  60

Pro Leu Ile Asn Pro Asn Phe Ile Glu Ile Asp Ser Ser Arg His Cys
 65                  70                  75                  80

Ala Glu Leu Ala Trp Asp Leu Asn Leu Pro Leu Pro Lys His Tyr Lys
                85                  90                  95

Phe Ile Tyr Ile Ser Pro His Gly Val Gly Ala Ala Phe Leu Arg
                100                 105                 110

Tyr Leu Asn Gln Cys Cys Asp Val Thr Cys Phe Ala Ser Trp Val Leu
         115                 120                 125

Pro Pro Asp Ser Lys Glu Arg Tyr Cys Ile Asn Tyr Met Cys Leu Asn
130                 135                 140

Asp Asn Thr Ile Ala Gln Tyr Ala Ile Asn Ile Ser Glu Ile Asn Leu
145                 150                 155                 160

Pro Tyr Phe Asp Lys Tyr Leu Ser Leu Leu Asp Phe Asn Ser Lys Ile
                165                 170                 175

Ile Cys Gly Val Arg Asp Pro Ile Gly Leu Leu Lys His Ser Trp Gly
                180                 185                 190

Arg Asp Trp Ser Lys Val Leu Arg Asn Tyr Pro Pro Glu Phe Asn Leu
         195                 200                 205

Thr Tyr Asp Trp Arg Tyr Tyr Ile Asn Tyr Leu Thr His Gln Asn His
210                 215                 220

Lys Ile Lys Ile Asp Ile Asn Glu Leu Gln Gln Gly Val Phe Ile Ile
225                 230                 235                 240

Ser Tyr Leu Leu Lys Tyr Phe Asn Lys Asp Asn Val Tyr Tyr Leu Asp
                245                 250                 255

Met Glu Glu Ile Arg Gln Ser Lys Ala Phe Asp Thr Met Asn Leu Leu
                260                 265                 270

Ala Ile Asn Phe Asn Phe Thr Pro Pro His Lys Asp Lys Leu Asp Leu
                275                 280                 285

Phe Lys Ile Lys Glu Phe Arg Gly Tyr Ile Arg Tyr Leu Phe Pro Ile
         290                 295                 300

Thr Leu Tyr Ala Asn Ser Lys Asp Ile Asn Asn Thr Phe Tyr Leu Asn
305                 310                 315                 320

Thr Pro Lys Asn Asn Lys Asn Phe Asn Ile Asp Arg Thr Ser Ser Ile
                325                 330                 335

Pro Ile Ile Leu Asp Arg Lys His Ile Asn His Glu Lys Ile Asp Ile
                340                 345                 350

Ile Gln Glu Ile Ile Lys Asn Asp Leu Cys Asn Asp Met Gly Val Tyr
         355                 360                 365
```

-continued

```
Ile Asp Lys Asn Asp Phe Lys Gln Leu Glu Gln Asn Asn Leu Leu Phe
    370             375             380

Ser Thr Ile Lys His Tyr Leu Tyr Asp Phe Leu Tyr Gln Ile Lys Ile
385             390             395             400

Thr Ile Asp Glu Thr Glu Ser Lys Met Met Lys Glu Lys Asp Val Ile
            405             410             415

Asp Tyr Phe Ile Lys Asn Lys Ser Leu Ile Tyr Thr Phe Phe Asn Ile
        420             425             430

Phe Glu Asn Glu Leu Asn His Leu Lys Gln Thr His Pro His Ile Ile
        435             440             445

Asp Ser Trp Lys Tyr Tyr Lys Glu Phe Glu Lys Ile Tyr Lys Asp Lys
    450             455             460
```